United States Patent [19]

El Khadem et al.

[11] 4,282,349
[45] Aug. 4, 1981

[54] CRYSTALLINE RIBOFURANOSYL HALIDES AND OTHER DERIVATIVES AND METHODS FOR PRODUCING SAME

[75] Inventors: Hassan S. El Khadem, Houghton, Mich.; Thakur D. Audichya, Poona, India; John Kloss, Gurnee, Ill.

[73] Assignee: Board of Control of Michigan Technological University, Houghton, Mich.

[21] Appl. No.: 951,969

[22] Filed: Oct. 16, 1978

Related U.S. Application Data

[63] Continuation of Ser. No. 750,265, Dec. 13, 1976, abandoned.

[51] Int. Cl.$^3$ .................... C07H 15/02; C07H 15/18; C07H 13/02
[52] U.S. Cl. ........................................ 536/4; 536/119; 536/55; 536/122
[58] Field of Search .............................. 536/4, 119, 55

[56] References Cited

U.S. PATENT DOCUMENTS

| | | | |
|---|---|---|---|
| 3,183,247 | 5/1965 | Kiss et al. | 536/4 |
| 3,277,077 | 10/1966 | Holly et al. | 536/55 |
| 3,419,544 | 12/1968 | Witzel et al. | 536/119 |
| 3,480,613 | 11/1969 | Walton | 536/119 |
| 3,501,456 | 3/1970 | Shen et al. | 536/55 |

OTHER PUBLICATIONS

Wolfrom, "Advances in Carbohydrate Chem.", vol. 21, pp. 300–303, Academic Press, New York, N.Y., 1966.
Wolfrom, "Advances in Carbohydrate Chem.", vol. 22, pp. 155–159, Academic Press, New York, N.Y., 1967.
Ness et al. "Chem. Abst.", vol. 75, 1971, p. 141081n.
El Khadem, et al. "Chem. Abst.", vol. 83, 1975, pp. 147,674v.
El Khadem, et al. "Chem. Abst.", vol. 84, 1976, pp. 180,490a.

*Primary Examiner*—Johnnie R. Brown
*Assistant Examiner*—Blondel Hazel

[57] ABSTRACT

Methyl-D-ribofuranoside is p-nitrobenzoylated to yield crystalline methyl 2,3,5-tri-O-(p-nitrobenzoyl)-β-D-ribofuranoside which can be used to prepare a stable, crystalline 2,3,5-tri-O-(p-nitrobenzoyl)-β-D-ribofuranosyl bromide which in turn is useful as a precursor of natural or synthetic purine and pyrimidine nucleosides, as well as of glycosides. This bromide can also be cyanated to yield crystalline 2,5-anhydro-3,4,6-tri-O-(p-nitrobenzoyl)-D-allononitrile which in turn can be hydrolyzed and subsequently reacted with polyamino pyrimidines to yield nucleoside analogs such as 8-β-D-ribofuranosyl adenine. This bromide also can by hydrolyzed to yield crystalline 2,3,5-tri-O-(p-nitrobenzoyl)-D-ribofuranose which in turn can be p-nitrobenzolated to yield crystalline 1,2,3,5-tetra-O-(p-nitrobenzoyl)-β-D-ribofuranose. This latter compound can be brominated to produce an alphabromide derivative which is useful as a precursor of nucleosides.

14 Claims, No Drawings

CRYSTALLINE RIBOFURANOSYL HALIDES AND OTHER DERIVATIVES AND METHODS FOR PRODUCING SAME

CROSS REFERENCE TO RELATED APPLICATIONS

This application, a continuation of application Ser. No. 750,265, filed Dec. 13, 1976 and now abandoned.

BACKGROUND OF THE INVENTION

This invention relates to novel ribofuranosyl derivatives and methods for preparing same.

Because of the interest in naturally occurring nucleosides, considerable effort has been directed towards synthesizing D-ribofuranosyl derivatives of purines, pyrimidines and other nitrogenous bases. Pentofuranosyl halides are valuable synthetic intermediates for the preparation of nucleosides, nucleoside analogs, and glycosides. Crystalline halides are preferred for this purpose because they can be purified and stored. At present, the most widely used D-ribofuranosyl halides are 2,3,5-tri-O-benzoyl-D-ribofuranosyl chloride and 2,3,5-tri-O-benzoyl-D-ribofuranosyl bromide, both of which are syrups obtained from crystalline precursors, such as 1-O-acetyl-2,3,5-tri-O-benzoyl-$\beta$-D-ribofuranose. These syrups are relatively unstable and, consequently cannot be stored, requiring them to be used immediately after preparation. Also, these syrups are difficult to purify. Furthermore, the processes employed to prepare these syrup halides requires several steps. Generally, attempts to prepare crystalline halides have either resulted in the production of syrupy products or require processes which are lengthy and involve several steps.

A principal object of the invention is to provide stable crystalline ribofuranosyl halides suitable for use in the preparation of nucleosides and related compounds and methods for preparing same.

Another object of the invention is to provide a stable crystalline ribofuranosyl precursor to these halides which may be used as intermediates in the preparation of these halides.

A further object of the invention is to provide a simplified method for preparing a stable crystalline ribofuranosyl bromide at relatively high yields.

A still further object of the invention is to provide crystalline derivatives of these halides which can be used as intermediates in the preparation of synthetic nucleosides and glycosides and methods for preparing same.

Other objects, aspects and advantages of the invention will become apparent upon reviewing the following detailed description and the appended claims.

According to the invention, a ribofuranosyl derivative capable of yielding a halide derivative thereof is first formed from methyl-D-ribofuranosyl and this derivative is blocked with a functional group which produces a crystalline derivative. More specifically, methyl-D-ribofuranoside is reacted with a p-nitrobenzoyl halide to effect the p-nitroenzoylation of the three free hydroxyl groups and yield a crystalline methyl-2,3,5-tri-O-(p-nitrobenzoyl)-$\beta$-D-ribofuranoside which can be halogenated to yield a crystalline 2,3,5-tri-O-(p-nitrobenzoyl)-$\beta$-D-ribofuranosyl halide.

The crystalline halide can be used in the synthesis of nucleosides and glycosides. Further, by cyanating under anhydrous conditions it can yield 2,5-anhydro-3,4,5-tri-O-(p-nitrobenzoyl)-D-allononitrile. Hydrolyzing this allononitrile yields 2,5-anhydro-D-allonic acid and this acid can be reacted with 4,5,6-triamino pyrimidine to yield 8-$\beta$-D-ribofuranosyl adenine.

This crystalline halide also can be used to prepare an alpha-halide precursor by first hydrolyzing it to yield the crystalline 2,3,5-tri-O-(p-nitrobenzoyl)-D-ribofuranose and p-nitrobenzoylating this ribofuranose to yield crystalline 1,2,3,5-tetra-O-(p-nitrobenzoyl)-$\beta$-D-ribofuranose which can be treated with an equimolar amount of a halide, such as hydrogen bromide in solution to yield an alpha-halide, such as 2,3,5-tri-O-(p-nitrobenzoyl)-$\beta$-D-ribofuranosyl bromide. Thus, the novel halides of the invention are the beta or alpha halide precursors for nucleosides.

DETAILED DESCRIPTION

The overall reaction sequence of preferred processes for preparing the various novel crystalline ribofuranosyl derivatives of the invention can be represented as follows:

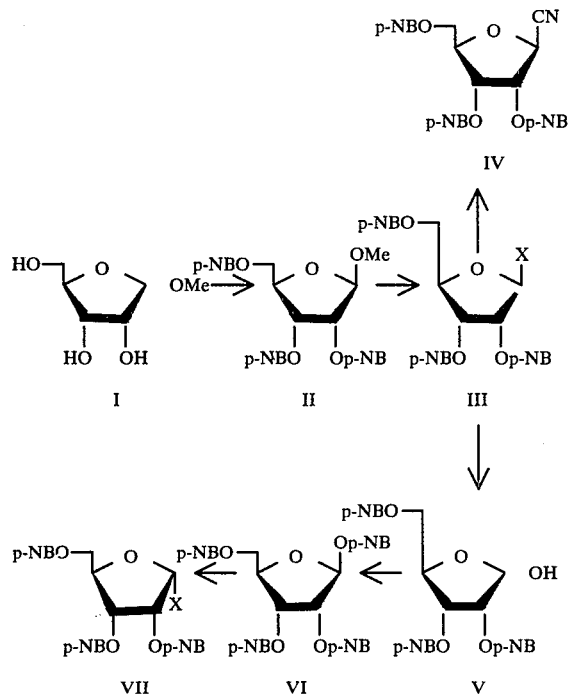

wherein Me is a methyl group, p-NB is a p-nitrobenzoyl group and X is a halogen, preferably bromine.

The starting compound (I), methyl-D-ribofuranoside, can be prepared in a conventional manner. For instance, it can be prepared in the manner described in the *Journal of the American Chemical Society*, Vol. 76, pages 763–767 (1953), namely, reacting D-ribose with methanolic hydrogen chloride for a sufficient time, e.g., 90 minutes, at room temperature to obtain a yellow syrup. Methyl-D-ribofuranoside is reacted with a p-nitrobenzoyl halide, such as p-nitrobenzoyl chloride. The p-nitrobenzoyl groups replace the hydrogen of the free hydroxyl groups of methyl-D-ribofuranoside and the novel crystalline compound II, 2,3,5-tri-O-(p-nitrobenzoyl)-$\beta$-D-ribofuranoside, is produced.

The syrupy methyl-D-ribofuranoside preferably is diluted with a suitable organic solvent, such as pyridine, chloroform and mixtures thereof, prior to the addition of the p-nitrobenzoyl halide and the initial p-nitrobenzoylation reaction preferably is carried out at a reduced temperature in order to prevent side reactions. As a guide, the diluted methyl-D-ribofuranoside can be cooled to a temperature of about 0° to 5° C. and the p-nitrobenzoyl halide is added thereto in incremental proportions with stirring at a rate whereby the temperature of the reaction mixture does not exceed about 5° to 10° C. After the p-nitrobenzoyl halide has been added, the reaction mixture can remain at room temperature until the reaction is completed, which usually takes about 5 to 20 hours.

After completion of the reaction, the reaction mixture is cooled to a temperature of about 0° to 5° C., ice is added to the cooled reaction mixture and the aqueous phase removed, such as by extracting with a suitable solvent, e.g., dichloromethane. The extract is evaporated under a reduced pressure to remove any remaining solvent and the solid residue is dissolved in a suitable solvent, such as dichloromethane, the resultant solution is washed, such as with successive treatments with a saturated solution of sodium hydrogen carbonate, water, a dilute solution of sulfuric acid, and water to remove such contaminants as p-nitrobenzoic acid, pyridine, etc. The washed solution is dried and evaporated under reduced pressure to produce a solid product which can be recrystallized from a suitable solvent, such as acetone-petroleum ether, to obtain substantially pure, crystalline methyl 2,3,5-tri-O-(p-nitrobenzoyl)-$\beta$-D-ribofuranoside (II).

The ribofuranoside (II) can be halogenated under reaction conditions whereby the methyl group thereof is replaced by a halogen so as to yield the novel crystalline halides (III). For example, to prepare the preferred bromide, the ribofuranoside (II) is dissolved in an organic solvent, such as dichloromethane, and then brominated, preferably by adding a solution of hydrogen bromide and some acetic acid to the solution. This bromination should be carried out under substantially anhydrous conditions in order to prevent hydrolysis. Therefore, the solvent preferably should be anhydrous and, as an added precaution, a small quantity of acetyl bromide can be added to the solution prior to bromination. The acetyl bromide reacts with any of the water in the solution to give acetic acid and hydrogen bromide. Also, the acetic acid used as the brominating medium preferably is treated to remove any water prior to addition of hydrogen bromide, such as by distilling over boron triacetate.

The solution is cooled to a reduced temperature of about 0° to 5° C. prior to addition of the brominating solution and the reaction mixture is thereafter maintained at a reduced temperature in the same general range until the reaction is completed, which generally takes about 10 hours to 5 days. After completion of the reaction, the acetic acid is carefully removed from the reaction mixture, such as by evaporation at room temperature and under reduced pressure, to yield a syrup. Any residual acetic acid is then removed from the syrup, such as by evaporation with dichloromethane/toluene to obtain the crystalline bromide, 2,3,5-tri-O-(p-nitrobenzoyl)-$\beta$-D-ribofuranosyl bromide. The crystals preferably are washed, such as with anhydrous diethyl ether, and then dried under a vacuum. The resultant crystals can be recrystallized, such as from dichloromethane, to obtain a pure crystalline bromide which is stable and can be kept up to 12 months at 0° C.

When pentofuranosyl halides other than the bromide are desired, the ribofuranoside (II) is reacted with another appropriate halide, such as hydrogen chloride.

The halide (III) can be reacted with a cyanide under reaction conditions whereby the halide thereof is replaced by cyanide so as to yield the novel crystalline compound (IV), 2,5-anhydro-3,4,6-tri-O-(p-nitrobenzoyl)-D-allononitrile. For example, 2,3,5-tri-O-(p-nitrobenzoyl)-$\beta$-D-ribofuranosyl bromide can be added to a moisture free suspension containing a suitable cyanide, such a mercuric cyanide. It is important that this reaction is carried out under strict anhydrous conditions to prevent hydrolysis. Accordingly, the cyanide preferably is first heated to an elevated temperature, e.g., 90° C., under a vacuum for an extended time period, e.g., 5 hours, to remove any moisture. Also, the dried cyanide preferably is formed into a suspension, such as by adding to nitromethane or benzene or mixtures thereof and the suspension is partially distilled to remove any last traces of moisture. After the remaining suspension has been cooled to a temperature of 0° to 10° C., the crystalline bromide is added thereto and the resultant mixture is allowed to stand under anhydrous conditions at room temperature until the reaction goes to completion which generally will take about 24 to about 78 hours.

The reaction mixture is then filtered into an aqueous solution of potassium bromide and an organic solvent to remove the mercury salts. The remaining mixture is then filtered, the filtrate extracted and the extract washed and dried over an anhydrous dehydrating material, such as magnesium sulfate, and then evaporated under reduced pressure to produce a yellow syrup. This syrup can be dissolved in a suitable organic solvent, such as dichloromethane, benzene, dichloromethane, carbontetrachloride and mixtures thereof, and the mixture allowed to stand at a reduced temperature of about 5° to 10° C. to crystallize out the allononitrile (IV). These crystals can be purified by recrystallization from a suitable solvent, such as dichloromethane.

The allononitrile (IV) can be hydrolyzed in a suitable manner, e.g., dissolved in a suitable solvent, such as dioxane, and heated in the presence of a relatively weak aqueous acid or alkaline solution to yield 2,5-anhydroallonic acid which is a precursor of 8-$\beta$-D-ribofuranosyl adenine.

The halide (III) can be hydrolyzed under reaction conditions when the halide thereof is replaced by a hydroxyl group so as to yield the novel crystalline compound (V), 2,3,5-tri-O-(p-nitrobenzoyl)-D-ribofuranose. For example, 2,3,5-tri-O-(p-nitrobenzoyl)-$\beta$-D-ribofuranosyl bromide can be dissolved in a suitable solvent, such as acetone, dichloromethane, or mixtures thereof, the solution cooled to a temperature of about 5° to 10° C., and then treated with an aqueous suspension of silver carbonate with vigorous stirring. The reaction mixture is filtered to remove residual solids and the filtrate is evaporated under a reduced pressure to yield a syrup from which the ribofuranose (V) is yielded in the form of colorless needles after dissolution in a suitable solvent, such as dichloromethane and recrystallization.

The ribofuranose (V) can be p-nitrobenzoylated to yield the novel crystalline compound (VI), 1,2,3,5-tetra-O-(p-nitrobenzoyl)-$\beta$-D-ribofuranose. For example, the ribofuranose (V) is dissolved in a suitable solvent, such as a mixture of chloroform and pyridine, the solution cooled to about 5° to 10° C., and a p-nitrobenzoyl halide, such as p-nitrobenzoyl chloride is slowly added to the cooled solution in a manner to prevent a significant increase in the temperature of the reaction mixture. The organic portion of the reaction mixture is then evaporated under a reduced pressure to form a syrup from which the ribofuranose (VI) is yielded as crystals after dissolution in a suitable solvent, such as dichloromethane, drying and redissolution.

An alpha-halide precursor of nucleosides can be prepared from the ribofuranose (VI) by halogenating same, such as by reacting with an equimolar amount of hydrogen bromide dissolved in dichloromethane, to yield the alphabromide nucleoside precursor (VII) 2,3,5-tri-O-(p-nitrobenzoyl)-α-D-ribofuranosyl bromide.

Without further elaboration, it is believed one skilled in the art can, by using the preceding description, utilize the present invention to its fullest extent. The following specific examples are presented for purposes of illustration and should not be construed to limit the invention to the specific features of these examples. In all these examples, melting points were determined on a Kofler block, nuclear magnetic resonance (NMR) spectra were recorded on a Varian T-60 instrument, and infrared spectra were recorded on a Perkin-Elmer PE-700 spectrometer.

EXAMPLE 1

Methyl-2,3,5-tri-O-(p-nitrobenzoyl)-β-D-ribofuranoside ($C_{27}H_{21}N_3O_{14}$)

12.5 g of D-ribose were dissolved in 250 ml of anhydrous methanol and 25 ml of anhydrous methanol containing 1.11 g of HCl were admixed therewith. The mixture was left at room temperature for 90 min and 25 ml of pyridine was then added to quench the reaction. The solution was evaporated to yield a yellow syrup, after which another 25 ml portion of pyridine was added and the evaporation process repeated. The yellow syrup (methyl-D-ribofuranoside) was diluted with 300 ml of pyridine and 100 ml of chloroform. While stirring rapidly, the reaction mixture was cooled to 0° C. and 50 g of p-nitrobenzoyl chloride were added over the course of 90 minutes during which time the reaction temperature was never allowed to exceed 10° C. The reaction mixture was slowly stirred while being maintained at room temperature for 15 hours.

The mixture was then cooled to 0° C. and 300 g of ice were added with increased stirring over the course of 60 minutes. The aqueous layer was separated and extracted twice with 25 ml portions of dichloromethane. The extracts were combined and evaporated under reduced pressure to remove most of the pyridine. The resulting solid residue was dissolved in 500 ml of dichloromethane. The solution was successively washed with a saturated solution of sodium hydrogen carbonate (4×200 ml), water (4×200 ml), ice-cold 1.5 M sulfuric acid (2×150 ml), and water (2×200 ml), dried with anhydrous magnesium sulfate, filtered, and then evaporated to dryness under reduced pressure. The solid product was then triturated with anhydrous diethyl ether and left to air dry. The resulting crystals were recrystallized from acetone-petroleum ether which yielded 44.5 g (86% yield) of methyl-2,3,5-tri-O-(p-nitrobenzoyl)-β-D-ribofuranoside in the form of light yellow needles and having a melting point of 169.5° to 170° C.

Elemental analysis of this product gave the following results: Calculated weight % for $C_{27}H_{21}N_3O_{14}$: C=53.04, H=3.46, N=6.87; Found weight %: C=53.08, H=3.45, N=6.66.

NMR analysis of the products was consistent with the assigned structure for the ribofuranoside (II) above. The infrared spectrum of the product showed no absorbance between 3600 and 3200 cm$^{-1}$ which confirmed the lack of a free hydroxyl and indicated tri-acyl substitution of the ribofuranoside. The other absorbances were due mainly to the p-nitrobenzoyl groups. Absorbances were assigned as follows: The absorbance at 1730 cm$^{-1}$ was assigned to the C=O stretching of the p-nitrobenzoyl groups, the absorbance at 1605 cm$^{-1}$ was due to one of the four bands indicative of an aromatic structure, the absorbances at 1520 cm$^{-1}$ and 1270 cm$^{-1}$ were assigned to the conjugated NO$_2$ asymmetric and symmetric stretching, respectively, the absorbance at 1350 cm$^{-1}$ was assigned to the aromatic C—NO$_2$ stretching and the absorbance at 870 cm$^{-1}$ was assigned to the aromatic C—N stretching.

EXAMPLE 2

2,3,5-tri-O-(p-nitrobenzoyl)-β-D-ribofuranosyl bromide ($C_{16}H_{18}N_3O_{13}Br$)

7.25 g of methyl-2,3,5-tri-O-(p-nitrobenzoyl)-β-D-ribofuranoside prepared by the procedure described in Example 1 were dissolved in 40 ml of anhydrous dichloromethane, the solution was cooled to 0° and then treated with 5 ml of acetyl bromide and 75 ml of a saturated solution of hydrogen bromide in acetic acid. The acetic acid was purified prior to use by reacting it with boron triacetate according to the method described in *The Synthesis and Characterization of Inorganic Compounds*, p. 116, Prentice-Hall, Englewood Cliffs, N.J. (1970). The reaction mixture was maintained at 4° for five days after which it was evaporated at room temperature under reduced pressure to yield an orange syrup. The syrup was slowly coevaporated twice with 25 ml portions of dry benzene and then twice with a mixture which contained 20 ml of dry benzene and 20 ml of dry toluene to yield light yellow crystals. These crystals were washed with anhydrous diethyl ether and allowed to dry overnight under high vacuum. This yielded 6.19 g (79% yield) of 2,3,5-tri-O-(p-nitrobenzoyl)-β-D-ribofuranosyl bromide. Recrystallization of this from dichloromethane yielded needles which had a melting point of 100° to 105° C.

Elemental analysis of this product gave the following results: Calculated weight % for $C_{26}H_{18}N_3O_{13}Br$: C=47.29, H=2.75, N=6.36; Found weight %: C=47.15, H=2.74, N=6.36.

NMR analysis of the product was consistent with the assigned structure for the bromide (III) above. The infrared spectrum of the product showed absorbances indicative of the p-nitrobenzoyl blocking groups. The absorbance at 1730 cm$^{-1}$ was assigned to the C=O stretching of the p-nitrobenzoyl group, the absorbance at 1605 cm$^{-1}$ was assigned to one of the four band indicative of an aromatic structure, the absorbances at 1520 cm$^{-1}$ and 1270 cm$^{-1}$ were assigned to the conjugated NO$_2$ asymmetric and symmetric stretchings, respectively, the absorbance at 1350 cm$^{-1}$ was assigned to the aromatic C—NO$_2$ stretch and the absorbance at 870 cm$^{-1}$ was assigned to the aromatic C—N stretching.

EXAMPLE 3

2,5-anhydro-3,4,6-tri-O-(p-nitrobenzoyl)-D-allononitrile ($C_{24}H_{18}N_4O_{13}$)

A suspension of 20 g of a mercuric cyanide (dried at 90° C. for five hours under high vacuum) in 75 ml of nitromethane was distilled with 20 ml of benzene until 25 ml of the distillate was collected to remove all moisture. The suspension was then cooled to 5° C. and 10 g of 2,3,5-tri-O-(p-nitrobenzoyl)-β-D-ribofuranosyl bromide prepared by the procedure described in Example 2 were added. The mixture was stirred at room temperature for 65 hours and then filtered into a mixture of 200 ml of cold, aqueous M potassium bromide and 40 ml of methanol to remove the mercury salts. After stirring for 30 min, the suspension was filtered and the filtrate extracted with ten 40 ml portions of dichloromethane. The extracts were combined, successively washed with three 40 ml portions of M potassium bromide, 50 ml of water, dried over anhydrous magnesium sulfate, and evaporated under reduced pressure to yield a syrup. Crystallization of this syrup from chloroform-carbon tetrachloride yielded 1.29 g (14% yield) of 2,5-anhydro-3,4,5-tri-O-(p-nitrobenzoyl)-D-allononitrile as needles which had a melting point of 105° to 108° C.

Elemental analysis of this product gave the following results: Calculated weight % for $C_{24}H_{18}N_4O_{13}$: C=53.47, H=2.99, N=9.24; Found weight %: C=53.34, H=3.09, N=9.14.

NMR analysis of this product was consistent with the assigned structure for allononitrile (IV) above. The infrared spectrum of the product, showed no significant changes from those of the compounds prepared in Examples 1 and 2.

Hydrolysis of this product yielded 2,5-anhydroallonic acid and reaction of this acid with 4,5,6-triamino pyrimidine, after cyclization, yielded the nucleoside, 8-β-D-ribofuranosyl adenine.

EXAMPLE 4

2,3,5-tri-O-(p-nitrobenzoyl)-D-ribofuranose ($C_{26}H_{19}N_3O_{14}.0.5H_2O$)

3 g of 2,3,5-tri-O-(p-nitrobenzoyl)-β-D-ribofuranosyl bromide prepared by the procedure described in Example 2 were dissolved in a mixture of 25 ml of acetone and 25 ml of dichloromethane. This solution was cooled to 5° C. and treated with a suspension of silver carbonate (1.25 g) in water (5 ml) with vigorous stirring. Stirring was continued for 90 minutes while the mixture was maintained at 5° C. The mixture was filtered and the filtrate evaporated under reduced pressure to yield a syrup. This syrup was redissolved in 50 ml of dichloromethane, dried over anhydrous MgSO₄ and evaporated to yield a syrup which solidified on slow coevaporation with benzene. This yielded 1.76 g (65% yield) of 2,3,5-tri-O-(p-nitrobenzoyl)-D-ribofuranose. Recrystallization of this product from nitromethane yielded colorless needles which had a melting point of 177° to 178° C.

Elemental analysis of the product gave the following results: Calculated weight % for $C_{16}H_{19}N_3O_{14}.0.5H_2O$: C=51.09, H=3.32, N=6.93; Found weight %: C=51.30, H=3.15, N=6.83.

NMR analysis of the product was consistent with the assigned structure for compound (V) above. The infrared spectrum of the product showed no significant changes from those of the compounds prepared in Examples 1, 2 and 3.

EXAMPLE 5

1,2,3,5-tetra-O-(p-nitrobenzoyl)-β-D-ribofuranose ($C_{33}H_{22}N_4O_{17}$)

2 g of powdered 2,3,5-tri-O-(p-nitrobenzoyl)-D-ribofuranose prepared by the procedure described in Example 4 were dissolved in a mixture of 10 ml of chloroform and 30 ml of pyridine and this solution was cooled to 5° C. and stirred. 0.65 g of p-nitrobenzoyl chloride were added slowly to the cooled solution with stirring over the course of 1 hour to insure that the temperature of the reaction mixture never exceeded 8° C. Stirring of the mixture was continued for 5 hours while the temperature was maintained at 15° C. The mixture was then cooled to 5° C. and 30 g of ice were added over the course of 90 minutes. The aqueous layer was separated and extracted with two 10 ml portions of dichloromethane. The extracts were combined with the organic layer of the reaction mixture and evaporated under reduced pressure to yield a syrup.

The syrup was redissolved in 50 ml of dichloromethane and the solution was successively washed with two 15 ml portions of an ice-cold, saturated solution of sodium hydrogen carbonate, two 15 ml portions of ice-cold water, one 10 ml portion of ice-cold 1.5 M sulfuric acid and two 15 ml portions of ice-cold water, dried with magnesium sulfate, filtered, and evaporated under reduced pressure to yield a syrup. The syrup was then dissolved in a few ml of anhydrous dichloromethane and left to crystallize overnight at 4° C. This yielded 0.5 g (20% yield) of 1,2,3,5-tetra-O-(p-nitrobenzoyl)-β-D-ribofuranose which had a melting point of 199° to 201° C.

Elemental analysis of the product gave the following results: Calculated weight % for $C_{33}H_{22}N_4O_{17}$: C=53.09, H=2.97, N=7.50; Found weight %: C=52.58, H=2.97, N=7.42.

NMR analysis of the product was consistent with the structure assigned to the ribofuranose (VI) above. The infrared spectrum of the product was quite similar to those of the compounds prepared in Examples 1-4.

Treatment 1,2,3,5-tetra-O-(p-nitrobenzoyl)-β-D-ribofuranose with an equimolar amount of HBr in dichloromethane at 0° for 5 hours afforded the crystalline 2,3,5-tri-O-(p-nitrobenzoyl)-α-D-ribofuranoside bromide.

From the foregoing description, one skilled in the art can easily ascertain the essential characteristics of this invention, and without departing from the spirit and scope thereof, can make various changes and modifications of the invention to adapt it to various usages.

In addition to being useful for preparation of the various derivatives described above, the novel crystalline halides (III), particularly the bromide, can be used as the starting material for preparing a nucleoside in a conventional manner, such as by the procedures described in *Synthetic Procedures in Nucleic Acid Chemistry*, Vol. 1, pages 161 and 166, Interscience Publishers and by Davoll, Lythgoe and Todd in *Journal of the American Chemical Society*, page 967 et seq. (1948).

For example, 2,3,5-tri-O-(p-nitrobenzoyl)-β-D-ribofuranosyl bromide can be converted to the well-known nucleoside, adenosine, which has many well known uses by refluxing a suspension containing it and chloromercuri-6-benzimido-purine in xylene, filtering the reaction mixture while still hot, precipitating the filtrate with petroleum ether, dissolving the precipitated chloromercuri complex in methanol, treating the resulting solution with metallic sodium under refluxing, evaporating the methanol, dissolving the resulting residue in water and extracting with chloroform, and evaporating the chloroform layer to obtain adenosine which can be recrystallized from water. The alpha-bromide nucleoside precursor prepared in Example 5, 2,3,5-tri-O-(p-nitrobenzoyl)-α-D-ribofuranose bromide, can be converted to an alpha adenosine by the same general procedure.

We claim:

1. A crystalline ribofuranosyl derivative selected from the group consisting of methyl-2,3,5-tri-O-(p-nitrobenzoyl)-β-D-ribofuranoside, a 2,3,5-tri-O-(p-nitrobenzoyl)-D-ribofuranosyl halide, 2,5-anhydro-3,4,6-tri-O-(p-nitrobenzoyl)-D-allononitrile, 2,3,5-tri-O-(p-nitrobenzoyl)-D-ribofuranose, and 1,2,3,5-tetra-O-(p-nitrobenzoyl)-β-D-ribofuranose.

2. Crystalline methyl-2,3,5-tri-O-(p-nitrobenzoyl)-β-D-ribofuranoside.

3. Crystalline 2,3,5-tri-O-(p-nitrobenzoyl)-β-D-ribofuranosyl bromide.

4. Crystalline 2,5-anhydro-3,4,6-tri-O-(p-nitrobenzoyl)-D-allononitrile.

5. Crystalline 2,3,5-tri-O-(p-nitrobenzoyl)-D-ribofuranose.

6. Crystalline 1,2,3,5-tetra-O-(p-nitrobenzoyl)-β-D-ribofuranose.

7. A method for preparing crystalline methyl-2,3,5-trio-O-(p-nitrobenzoyl)-β-D-ribofuranoside comprising the steps of admixing a compound containing a p-nitrobenzoyl halide with a solution of methyl-D-ribofuranoside under reaction conditions whereby each of the three hydroxyl groups of the latter compound are replaced with a p-nitrobenzoyl group of the former compound, and crystallizing out methyl-2,3,5-tri-O-(p-nitrobenzoyl)-β-D-ribofuranoside from the resultant reaction mixture.

8. A method for preparing crystalline 2,3,5-tri-O-(p-nitrobenzoyl)-β-D-ribofuranosyl bromide comprising the steps of admixing a brominating agent with a solution of methyl-2,3,5-tri-O-(p-nitrobenzoyl)-β-D-ribofuranoside under anhydrous reaction conditions whereby the methyl group of the latter compound is replaced by bromide of the brominating agent, and crystallizing out said bromide from the resultant reaction mixture.

9. A method for preparing crystalline 2,5-anhydro-3,4,6-tri-O-(p-nitrobenzoyl)-D-allononitrile comprising the steps of admixing 2,3,5-tri-O-(p-nitrobenzoyl)-β-D-ribofuranosyl bromide with an anhydrous medium containing a cyanide compound under anhydrous reaction conditions whereby the bromide of the former compound is replaced by cyanide from the latter compound, and crystallizing out said allononitrile from the resultant reaction mixture.

10. A method for preparing crystalline 2,3,5-tri-O-(p-nitrobenzoyl)-D-ribofuranose comprising the steps of hydrolyzing a solution containing 2,3,5-tri-O-(p-nitrobenzoyl)-β-D-ribofuranosyl bromide under reaction conditions whereby the bromide thereof is replaced by a hydroxyl group, and crystallizing out said ribofuranose from the resultant reaction mixture.

11. A method for preparing crystalline 1,2,3,5-tetra-O-(p-nitrobenzoyl)-β-D-ribofuranose comprising the steps of admixing a p-nitrobenzoyl-halide with a solution of 2,3,5-tri-O-(p-nitrobenzoyl)-D-ribofuranose at a temperature less than ambient and under reaction conditions whereby the hydroxyl group of the latter compound is replaced by a p-nitrobenzoyl group of the former compounds, and crystallizing out 1,2,3,5-tetra-O-(p-nitrobenzoyl)-β-D-ribofuranose from the resultant reaction mixture.

12. A method for preparing crystalline 2,3,5-tri-O-(p-nitrobenzoyl-α-D-ribofuranosyl bromide comprising the steps of reacting 1,2,3,5-tetra-O-(p-nitrobenzoyl)-β-D-ribofuranose with equimolar amounts of a bromide.

13. A method for preparing a crystalline 2,3,5-tri-O-(p-nitrobenzoyl)-β-D-ribofuranosyl halide comprising the steps of admixing a compound containing a p-nitrobenzoyl halide with a solution of methyl-D-ribofuranoside under reaction conditions whereby each of the three hydroxyl groups of the latter compound are replaced with a p-nitrobenzoyl group of the former compound to obtain methyl-2,3,5-tri-O-(p-nitrobenzoyl-β-D-ribofuranoside;

admixing a halogenating agent with a solution of said methyl-2,3,5-tri-O-(p-nitrobenzoyl)-β-D-ribofuranoside under anhydrous reaction conditions whereby the methyl group of the latter compound is replaced by the halide of the halogenating agent; and crystallizing out said 2,3,5-tri-O-(p-nitrobenzoyl)-β-D-ribofuranosyl halide from the resultant reaction mixture.

14. A method according to claim 13 wherein said halogenating agent is a brominating agent and a crystalline 2,3,5-tri-O-(p-nitrobenzoyl)-β-D-ribofuranosyl bromide is obtained from the resultant reaction mixture.

* * * * *